(12) United States Patent
Yun et al.

(10) Patent No.: US 12,066,185 B2
(45) Date of Patent: Aug. 20, 2024

(54) SENSOR-BASED MONITORING DEVICE FOR PREVENTING EXPLOSION ACCIDENT OF REGENERATIVE THERMAL OXIDIZER (RTO)

(71) Applicant: TAESUNG ENVIRONMENTAL RESEARCH INSTITUTE CO., LTD., Ulsan (KR)

(72) Inventors: Gi Yeol Yun, Ulsan (KR); Seok Man Kim, Ulsan (KR); Nam Goo Moon, Ulsan (KR); Seong Hee Kang, Ulsan (KR)

(73) Assignee: TAESUNG ENVIRONMENTAL RESEARCH INSTITUTE CO., LTD., Ulsan (KR)

( * ) Notice: Subject to any disclaimer, the term of this patent is extended or adjusted under 35 U.S.C. 154(b) by 432 days.

(21) Appl. No.: 17/617,493

(22) PCT Filed: Dec. 10, 2020

(86) PCT No.: PCT/KR2020/018069
§ 371 (c)(1),
(2) Date: Dec. 8, 2021

(87) PCT Pub. No.: WO2022/102855
PCT Pub. Date: May 19, 2022

(65) Prior Publication Data
US 2022/0349578 A1 Nov. 3, 2022

(30) Foreign Application Priority Data
Nov. 13, 2020 (KR) .................. 10-2020-0151439

(51) Int. Cl.
*F23N 5/24* (2006.01)
*B01D 53/30* (2006.01)
*G01N 33/00* (2006.01)
*F23G 7/06* (2006.01)

(52) U.S. Cl.
CPC .............. *F23N 5/242* (2013.01); *B01D 53/30* (2013.01); *G01N 33/0036* (2013.01); *F23G 7/068* (2013.01)

(58) Field of Classification Search
CPC ......... F23G 7/068; B01D 53/30; F23N 5/003; F23N 5/242; G01N 33/0036
See application file for complete search history.

(56) References Cited

FOREIGN PATENT DOCUMENTS

| JP | 2013079778 A | 5/2013 |
|---|---|---|
| JP | 6024890 B2 | 11/2016 |
| KR | 20120039276 A | 4/2012 |
| KR | 20130039092 A | 4/2013 |
| KR | 10-2017-0023331 A | 3/2017 |
| KR | 20170023331 A | 3/2017 |
| KR | 10-1965437 B1 | 4/2019 |
| KR | 101965437 B1 | 4/2019 |

*Primary Examiner* — Ko-Wei Lin
(74) *Attorney, Agent, or Firm* — NKL LAW; Jae Youn Kim (57) ABSTRACT

According to an embodiment, a monitoring device, comprising: a sensor for sensing inflow gas information including a component and a concentration of an inflow gas introduced into a regenerative thermal oxidizer (RTO); and a processor for determining residual gas information including a component and a concentration of a residual gas in the RTO by using the inflow gas information, and updating an inflow amount per unit time of the inflow gas according to a risk level of the RTO determined based on the residual gas information, is provided.

7 Claims, 4 Drawing Sheets

| CONTROLLED MATTER / PH RANGE | NORMAL LEVEL | FIRST LEVEL | SECOND LEVEL | THIRD LEVEL | FOURTH LEVEL | FIFTH LEVEL |
|---|---|---|---|---|---|---|
| CONTROLLING INFLOW AMOUNT PER UNIT TIME OF INFLOW GAS | X (1-1 VALUE) | O (1-2 VALUE) | O (1-3 VALUE) | O (1-4 VALUE) | O (1-5 VALUE) | X |
| CHANGING COMPONENT OF INFLOW GAS | X (FIRST COMPONENT) | X (FIRST COMPONENT) | O (SECOND COMPONENT) | O (THIRD COMPONENT) | O (FOURTH COMPONENT) | X |
| CONTROLLING DISCHARGE AMOUNT PER UNIT TIME OF EXHAUST GAS | X (2-1 VALUE) | X (2-1 VALUE) | X (2-1 VALUE) | O (2-2 VALUE) | O (2-3 VALUE) | O (2-4 VALUE) |
| APPLYING NON-COMBUSTIBLE GAS | X | X | X | X | O | X |
| STOPPING GAS SUPPLY | X | X | X | X | X | O |

RISK LEVEL INCREASES →

SENSOR-BASED MONITORING DEVICE FOR PREVENTING EXPLOSION ACCIDENT OF REGENERATIVE THERMAL OXIDIZER (RTO)

TECHNICAL FIELD

The present invention relates to a sensor-based monitoring device for preventing explosion accidents of a regenerative thermal oxidizer (RTO). More specifically, the present invention relates to a device capable of stably controlling a process exhaust gas supplied to the RTO, preventing explosion accidents of RTO according to excessive supply of an exhaust gas caused by a sudden process abnormality, and supporting RTO to operate safely.

BACKGROUND ART

In general, substances such as volatile organic compounds (VOCs), total hydrocarbons (THCs), etc. are generated as a result of chemical reactions during processes in petrochemicals, reactors of refineries, distillation towers, storage tanks, etc., or exhaust gas is generated due to the increase of vapor pressure as a result of increase in reaction temperature or atmospheric temperature during storage.

Accordingly, for safe operation of the process, volatile organic compound (VOC) and total hydrocarbon (THC) gas are discharged by controlling the operating pressure, and the discharged gas is supplied to the regenerative thermal oxidizer (RTO), which is a heat-storage type combustion oxidation equipment, and combusted continuously at around 800° C. to 850° C. so as to prevent problems such as air pollution, odor, etc.

However, according to prior art, when a large amount of volatile organic compound (VOC) and total hydrocarbon (THC) gas is introduced as an unpredictable abnormal state of process suddenly occurs, there are problems such that back fire and explosion accidents may occur when RTO is overloaded and the lower explosive limit (LEL) is exceeded.

In addition, according to prior art, when a trip occurs due to a momentary power failure, etc., the residual amount of non-combustible gas and the content of gas supplied during the process cannot be confirmed at the time of restarting, and thus there are problems such that back fire and explosion accidents may occur when the explosion conditions of the combustible gas are met during the process of re-igniting the RTO.

In this regard, a demand for a technology capable of overcoming the above problems and preventing explosion accidents of RTO is gradually increasing.

SUMMARY OF INVENTION

Technical Task

An embodiment of the present invention aims at solving the above problems of prior art, and providing a device capable of stably controlling a gas supplied to the RTO, preventing explosion accidents of RTO caused by a sudden process abnormality, and supporting the RTO to operate safely.

The object of the present invention is not limited to the objects mentioned above, and other objects not mentioned can be clearly understood from the following description.

Means for Solving Technical Task

The monitoring device according to a first aspect of the present invention may comprise: a sensor for sensing inflow gas information including a component and a concentration of an inflow gas introduced into a regenerative thermal oxidizer (RTO); and a processor for determining residual gas information including a component and a concentration of a residual gas in the RTO by using the inflow gas information, and updating an inflow amount per unit time of the inflow gas according to a risk level of the RTO determined based on the residual gas information.

In addition, the processor may determine whether the risk level is greater than or equal to a predetermined level based on whether the concentration of a predetermined specific gas among the residual gas satisfies a predetermined first condition, or whether an inflow increase amount per unit time of the inflow gas satisfies a second condition.

In addition, when the risk level is greater than or equal to a predetermined level, the processor may be disposed at an inlet of the RTO to transmit a control signal for reducing the inflow amount per unit time of the inflow gas to a level equal to or lower than a predetermined value corresponding to the risk level to an inflow valve which adjusts the amount of inflow gas. In addition, the processor may determine at least one of controlling the inflow amount per unit time of the inflow gas, changing the component of the inflow gas, controlling the discharge amount per unit time of the exhaust gas discharged from the RTO, applying non-combustible gas to the RTO, and stopping the supply of gas to the RTO according to the risk level.

In addition, a higher priority may be granted in the order of controlling the inflow amount per unit time of the inflow gas, applying the non-combustible gas, changing the component of the inflow gas, controlling the discharge amount per unit time of the exhaust gas, and stopping the supply of gas.

In addition, when it is determined to change the component of the inflow gas, the processor may acquire gas scheduling information representing the component and the concentration of gas to be introduced to the RTO according to the flow of time based on history on the inflow gas information and the residual gas information for a predetermined time period, and control the component of the inflow gas and the inflow amount per unit time according to the gas scheduling information.

In addition, when a user input for restarting the RTO is received, the processor may determine the residual gas information based on the history on the inflow gas information and the residual gas information for a predetermined time period, determine a restart risk level based on the residual gas information, and determine whether to restart the RTO based on whether the restart risk level is greater than or equal to a predetermined level.

The monitoring method according to a second aspect of the present invention may comprise the steps of: sensing inflow gas information including the component and the concentration of the inflow gas introduced into a regenerative thermal oxidizer (RTO); determining residual gas information including the component and the concentration of residual gas in the RTO by using the inflow gas information; and updating the inflow amount per unit time of the inflow gas according to the risk level of the RTO determined based on the residual gas information.

A third aspect of the present invention may provide a computer program stored in a recording medium for implementing the method according to the second aspect. Alternatively, a fourth aspect of the present invention may provide a computer-readable recording medium in which a program for executing the method according to the second aspect on a computer is recorded.

Effect of Invention

An embodiment of the present invention is capable of stably controlling the gas supplied to the RTO, allowing a large amount of volatile organic compound and total hydrocarbon gas to be excessively introduced by a sudden process abnormality to prevent exceeding the lower explosive limit (LEL), preventing explosion accidents of RTO and supporting RTO to operate safely.

The effects of the present invention are not limited to the above-mentioned effects, and it should be understood that the effects of the present invention include all effects that could be inferred from the configuration of the invention described in the detailed description of the invention or the appended claims.

DETAILED MEANS FOR CARRYING OUT THE INVENTION

For the terms used in embodiments, general terms that are used widely at present have been selected as possible in consideration of the functions in the present invention, but this may vary according to the intention or precedent of a person skilled in the art, the emergence of new technologies and the like. In addition, in certain cases, there is also a term arbitrarily selected by the applicant, in which case the meaning will be described in detail in the description of the invention. Therefore, the terms used herein should be defined based on the meanings of the terms and the contents throughout the present invention, rather than the names of the simple terms.

Throughout the specification, when a part is said to "comprising" a component, this means that it may further include other components, except to exclude other components unless specifically stated otherwise. In addition, the terms " . . . unit," " . . . module," etc. described in the specification mean a unit for processing at least one function or operation, which is implemented into hardware or software or a combination of hardware and software.

As used herein, the term "providing" includes a process in which a subject obtains specific information, or directly or indirectly transmits or receives specific information to a specific object, and may be comprehensively interpreted as including performance of actions for achieving specific objects, and should not be limitedly interpreted. In addition, the term "supporting" may be comprehensively interpreted as including performance of actions for achieving specific objects, and should not be limitedly interpreted.

Hereinafter, the embodiments of the present invention will be described in detail to an extent to be easily carried out by a person skilled in the art with reference to the accompanying drawings. However, the present invention may be implemented in various different forms and is not limited to the embodiments described herein.

Hereinafter, the embodiments of the present invention will be described in detail with reference to the accompanying drawings.

Figure 1:
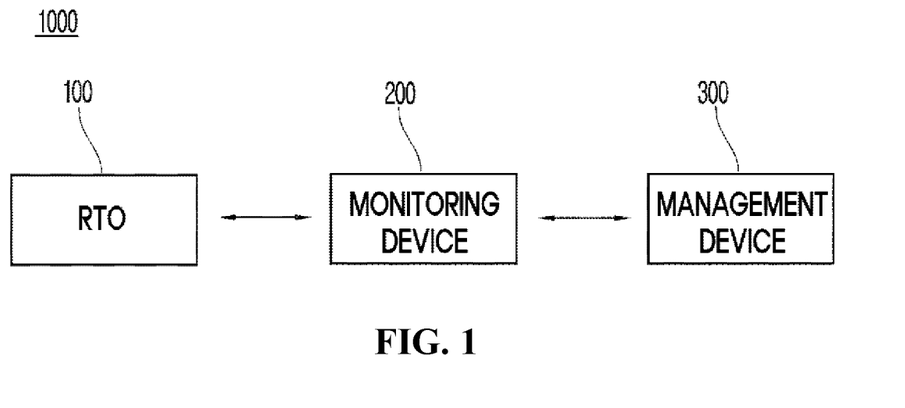
FIG. 1 is a schematic diagram illustrating the configuration of the RTO monitoring system according to an embodiment.

FIG. 1 is a schematic diagram illustrating the configuration of the RTO monitoring system 1000 according to an embodiment.

With reference to FIG. 1, the RTO monitoring system 1000 according to an embodiment may comprise one or more RTOs 100, one or more monitoring devices 200, and a management device 300.

The regenerative thermal oxidizer (RTO) 100 according to an embodiment represents a heat-storage type combustion oxidation equipment, and for example, incinerates harmful gas by continuously combusting the gas introduced to the inside according to a predetermined combustion temperature (e.g., 830° C. to 850° C.). According to an embodiment, the RTO 100 may comprise an inlet through which gas for combustion oxidation treatment is introduced, a distribution chamber for inducing the flow of gas, a heat storage layer for performing preheating and heat storage, a combustion furnace for performing combustion oxidation for gas, a flow controller (e.g., damper, rotary wing) for controlling the flow of gas, and an outlet for discharging gas subjected to combustion oxidation treatment.

The monitoring device 200 according to an embodiment corresponds to a device which may monitor the RTO 100. According to an embodiment, the monitoring device 200 may comprise an RTO 100, and for example, may be installed at one end of the RTO 100 to be implemented as an integrated RTO capable of controlling the overall operation of the RTO 100. According to another embodiment, the monitoring device 200 may be implemented as a server such as a computer, etc. operating through a computer program for realizing the functions described in the present specification, and for example, may be implemented as a server capable of remotely controlling the operation of each RTO 100 based on the gas information received from the plurality of sensors 210 respectively attached to the plurality of RTOs 100.

According to an embodiment, the monitoring device 200 may comprise all types of wired or wireless communication devices which may be connected to other devices (e.g., RTO, server, terminal) through a network, or have inner components connected. Here, the network may be configured through various communication networks such as wired and wireless networks, etc., and for example, may be configured through various communication networks such as a local area network (LAN), a metropolitan area network (MAN), a wide area network (WAN), etc.

The management device 300 according to an embodiment may be connected to the monitoring device 200 through a network, and for example, may perform integrated monitoring for a plurality of RTOs 100 based on the information received from a plurality of monitoring devices 200.

According to an embodiment, the management device 300 may comprise a management server (not shown) for performing integrated monitoring for one or more RTOs 100, and according to another embodiment, may comprise a manager terminal (not shown) corresponding to a manager account which receives information on one or more RTOs 100 from the monitoring device 200 implemented as a server. According to an embodiment, the manager terminal may be implemented as various types of handheld-based wireless communication devices such as a mobile phone, a smartphone, a personal digital assistant (PDA), a portable multimedia player (PMP), a tablet PC, etc., or may comprise various types of wired or wireless communication devices which may be connected to a vehicle report server for installing and executing applications such as a desktop PC, a tablet PC, a laptop PC, etc.

In addition, in addition to the components illustrated in FIG. 1, the RTO monitoring system 1000 may further comprise other generally used components. Alternatively, according to another embodiment, some of the components illustrated in FIG. 1 may be omitted.

Figure 2:
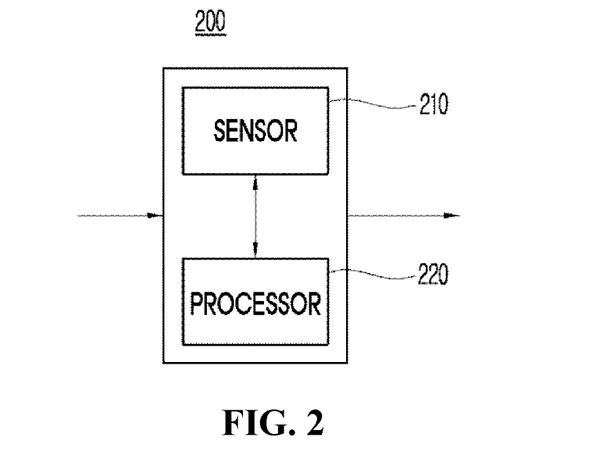
FIG. 2 is a block diagram illustrating the configuration of the monitoring device according to an embodiment.

FIG. 2 is a block diagram illustrating the configuration of the monitoring device 200 according to an embodiment.

With reference to FIG. 2, the monitoring device 200 according to an embodiment may comprise one or more sensors 210 and a processor 220.

The sensor 210 may sense inflow gas information including the component and the concentration of the inflow gas introduced into the RTO 100. According to an embodiment, the sensor 210 may comprise a first gas sensor for sensing the inflow gas, and the first gas sensor may be disposed at an inlet of the RTO 100 to sense, in a predetermined cycle, information on the component (e.g., volatile organic compound gas) and the concentration (e.g., amount of volatile organic compound gas per unit area) (e.g., 2,500 μg/Sm$^3$) of the harmful gas introduced into the RTO 100 through an inlet.

According to an embodiment, the inflow gas may include harmful gas introduced to the RTO 100, and for example, may include at least one of volatile organic compound (VOC) gas and total hydrocarbon gas, but is not limited thereto, and may include other various harmful gases whose harmfulness may decrease through combustion treatment such as hydrogen sulfide, hydrogen nitride, ammonia gas, etc.

According to an embodiment, the sensor 210 may further comprise at least one of a second gas sensor for sensing residual gas information including the component and the concentration of residual gas in the RTO 100, and a third gas sensor for sensing exhaust gas information including the component and the concentration of exhaust gas discharged from the RTO 100. For example, the second gas sensor may be disposed in at least one of the distribution chamber, the heat storage chamber and the combustion chamber of the RTO 100 to sense residual gas information, and as another example, the third gas sensor may be disposed at the outlet of the RTO 100 to sense exhaust gas information.

According to an embodiment, the residual gas includes harmful gas remaining in the RTO 100, and exhaust gas includes harmful gas discharged from the RTO 100. Throughout the specification, for the sake of convenience in explanation, different terms such as inflow gas, residual gas and exhaust gas have been described, but it may be understood as a concept distinguished according to a series of processes in which gas is introduced to the RTO 100 and subjected to combustion oxidation treatment, and then discharged.

According to an embodiment, the sensor 210 may sense at least one of the concentration of oxygen gas included in the inflow gas, the concentration of oxygen gas included in the residual gas, and the concentration of the oxygen gas included in the exhaust gas, and for example, may sense the component and the concentration of harmful gas included in the inflow gas and the concentration of oxygen gas, respectively. The information sensed as above may be used so that the processor 220 predicts a concentration ratio between combustibles and oxygen. Also, the sensor 210 may further comprise a sensor module for sensing the pressure, temperature, etc. of gas.

The processor 220 may determine residual gas information including the component and the concentration of the residual gas in the RTO 100 by using the inflow gas information. For example, the processor 220 may store and manage the inflow gas information received from the sensor 210 together with sensor identifier and reception time. In addition, the processor 220 may monitor the component and the amount of the gas introduced into the RTO 100 in real time according to the prestored concentration calculation algorithm, and determine predicted values of the component and the concentration of the residual gas remaining in the current RTO 100.

According to an embodiment, the processor 220 may determine the residual gas information at the current time by using the inflow gas information and the residual gas information stored during a predetermined time period. According to an embodiment, the processor 220 may calculate predicted values of the component and the concentration of residual gas in a way of predicting the flow of concentration of residual gas by using at least one of inflow amount per unit time for each gas component, amount of change in inflow amount per unit time, and immediately preceding concentration of residual gas (e.g., most recently predicted concentration of residual gas, initial setting value, etc.), and for example, may determine the concentration of propane gas (e.g., 1%, concentration ratio) remaining in the current RTO 100 based on the inflow amount per unit time of propane gas introduced to the RTO 100 during the first 30 minutes.

According to another embodiment, when residual gas information is received from the sensor 210, the processor 220 may update the residual gas information by using the inflow gas information, and for example, may determine a predicted value of the residual gas information at the current time by using the inflow gas information and the residual gas information stored during a predetermined time period, and correct the residual gas information by reflecting the predicted value to the sensed value when the difference between the sensed value and the predicted value of the residual gas information received from the sensor 210 is greater than or equal to a predetermined value.

According to an embodiment, the concentration of the residual gas may be represented by at least one of the proportion (e.g., 1%) of a target gas (e.g., propane gas) in the residual gas and the amount of target gas per unit area (e.g., 2,500 μg/Sm$^3$)

The processor 220 may determine the risk level of the RTO 100 based on the residual gas information. According to an embodiment, the processor 220 may determine whether the risk level is greater than or equal to a predetermined level based on whether the concentration of a predetermined specific gas among the remaining gas satisfies a predetermined first condition. For example, the processor 220 may determine that the risk level is greater than or equal to a predetermined level by determining that the explosive conditions are met when the current concentration (e.g., 3%) of a specific harmful gas (e.g., propane gas) among the residual gas is within a predetermined explosion threshold range (e.g., 2.1% to 9.5%) corresponding to the corresponding harmful gas. According to an embodiment, the explosion threshold range includes a lower explosive limit (LEL) and an upper explosive limit (HEL), and it may be determined that the explosive conditions are met when the concentration is between the lower explosion level and the upper explosion level.

According to an embodiment, the processor 220 may determine whether the risk level is greater than or equal to a predetermined level based on whether the inflow increase amount per unit time of inflow gas satisfies a predetermined second condition. For example, when the inflow amount per unit time (e.g., 2,500 μg/$Sm^3$*s) of the entire inflow gas or a specific harmful gas (e.g., propane gas) among the entire inflow gas is determined according to the inflow gas information, the processor 220 may determine the increase amount (e.g., Δ100 μg/$Sm^3$*s) of inflow amount per unit time by analyzing the change trend according to the flow of time with respect to the determined inflow amount per unit time, and determine that the risk level is greater than or equal to a predetermined level when the increase amount of inflow amount per unit time satisfies a predetermined explosive warning condition (e.g., >500 μg/$Sm^3$*s) corresponding to the entire inflow gas or corresponding harmful gas.

According to an embodiment, the processor 220 may determine the risk level of the RTO 100 by using the inflow gas information and the residual gas information received from the sensor 210, and for example, determine whether the concentration of a predetermined specific gas among the current residual gas satisfies a first condition according to the component and the concentration of residual gas received from the sensor 210, and determine whether the inflow increase amount per unit time of a specific gas among the current inflow gas satisfies a predetermined specific second condition according to the component and the concentration of inflow gas received from the sensor 210, thereby determining that the risk level is greater than or equal to a predetermined level when at least one of the conditions is satisfied.

According to an embodiment, the processor 220 may determine the risk level by granting a higher weight in the order of the first condition and the second condition. For example, when only the second condition is satisfied, the risk level is determined to be a first level, and when only the first condition is satisfied, the risk level is determined to be a second level which is higher than the first level, and when both the first condition and the second condition are satisfied, the risk level is determined to be a third level which is higher than the second level.

According to an embodiment, the processor 220 may determine the risk level by using at least one of the oxygen concentration in inflow gas, pressure and temperature in RTO 100. For example, by analyzing the inflow gas, the risk level may be updated to be higher according to how closely the oxygen concentration satisfies the combustion (explosion) condition, or updated to be higher as the pressure and temperature in the RTO 100 is greater than a predetermined reference value.

The processor 220 may update the inflow amount per unit time of inflow gas introduced to the RTO 100 according to the determined risk level, and for example, control the amount of gas supplied to the RTO 100 when it is predicted that a problem will occur according to the prediction result of risk levels.

In other words, in case the amount of gas introduced into the RTO 100 increases suddenly and excessively when the concentration of harmful gas in the RTO 100 is within an explosive threshold range, the proper amount which the RTO 100 may pull off per unit time would be exceeded, thereby increasing the explosion possibility as combustible gases enters the RTO 100 suddenly and excessively.

Accordingly, when a problem is sensed by monitoring the condition of the gas introduced to the RTO 100 in real time, the processor 220 may stably supply gas in a way that reduces the inflow amount of gas supplied to the RTO 100 so that the concentration of combustible gas in the RTO 100 is maintained below a lower explosive limit, and minimize the potential explosion possibility by maintaining the load of the RTO 100 to be low.

According to an embodiment, when the risk level is greater than or equal to a predetermined level, the processor 220 may transmit the control signal, which reduces the inflow amount per unit time of inflow gas to a predetermined value or below corresponding to the risk level, to an inflow valve (not shown) of the RTO 100. According to an embodiment, the inflow valve of RTO 100 may be disposed at an inlet of the RTO 100 introducing inflow gas and control the amount of inflow gas. For example, the amount of inflow gas introduced to the RTO 100 through an inflow passage per unit time may be controlled to decrease or increase by controlling the opening/closing area or opening/closing period of inflow passage connecting the outside and the inside of the RTO 100 according to the control signal of the processor 220.

According to an embodiment, the processor 220 may determine the inflow amount per unit time of inflow gas based on the concentration ratio of harmful gas included in the inflow gas. For example, in order to lower the concentration of propane gas (e.g., 3%) to a specific threshold value (e.g., 2.1%) or below, the inflow amount per unit time of the entire inflow gas may be inversely calculated from the target value (e.g., 1%) of the concentration ratio of propane gas in the inflow gas, and the opening/closing area of the inflow passage may be controlled accordingly.

According to an embodiment, the predetermined value for controlling the inflow amount per unit time of the inflow gas may vary depending on the type of gas and risk level, and for example, the predetermined value may be smaller as the risk level with respect to a specific type of gas is higher, and may be determined to be in inverse proportion to the risk level.

According to an embodiment, the processor 220 may control the RTO 100 differently according to the risk level. Details in this regard will be described with further reference to FIGS. 3 and 4.

Figure 3:
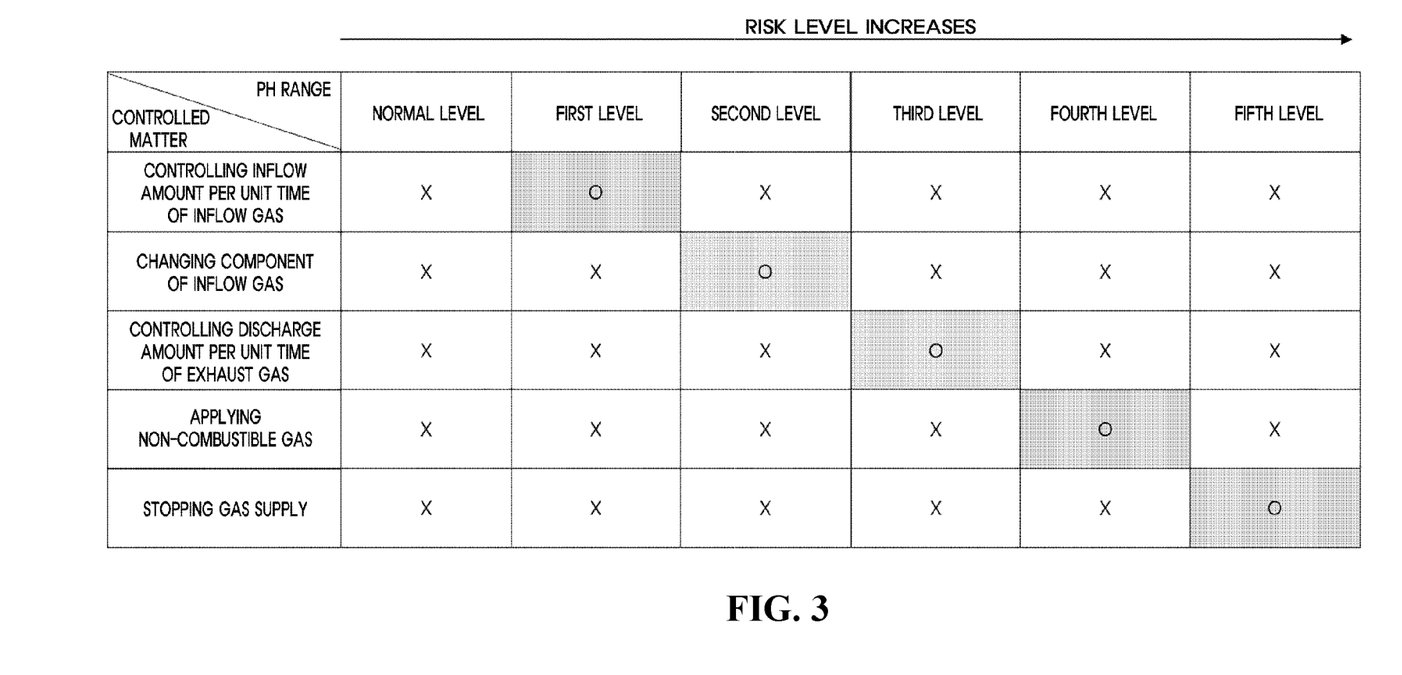
FIG. 3 is a view for explaining an operation of the monitoring device according to an embodiment to control RTO in different ways according to the risk level.
Figure 4:
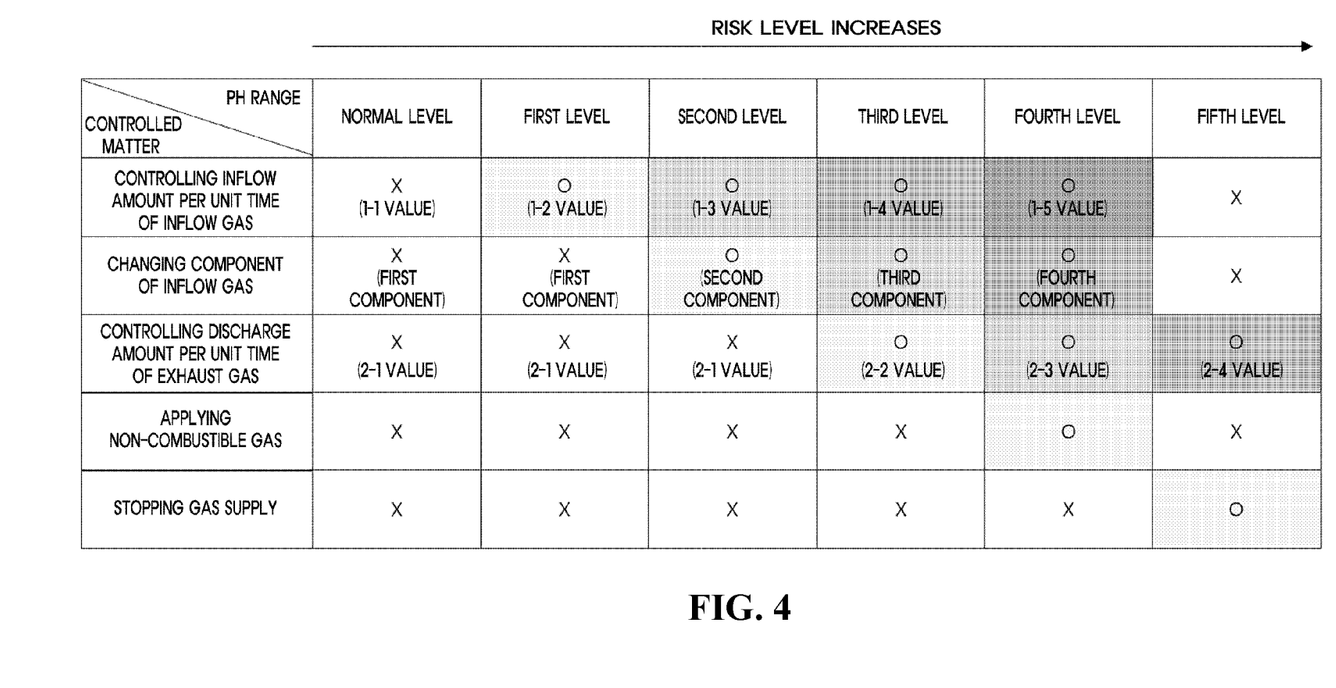
FIG. 4 is a view for explaining an operation of the monitoring device according to an embodiment to control RTO in different ways according to the risk level.

FIGS. 3 and 4 are views for explaining an operation of the monitoring device 200 according to an embodiment to control RTO 100 in different ways according to the risk level.

With reference to FIGS. 3 and 4, the processor 220 may determine at least one of controlling the inflow amount per unit time of the inflow gas, changing the component of the inflow gas, controlling the discharge amount per unit time of the exhaust gas discharged from the RTO 100, applying non-combustible gas to the RTO 100, and stopping the supply of gas to the RTO 100 according to the risk level.

With reference to FIG. 3, the processor 220 may grant a higher priority in the order of controlling the inflow amount per unit time of the inflow gas, applying the non-combustible gas, changing the component of the inflow gas, controlling the discharge amount per unit time of the exhaust gas, and stopping the supply of gas while controlling according to risk level. For example, as illustrated in FIG. 3, the processor may operate in the order of controlling the inflow amount per unit time of the inflow gas, changing the component of the inflow gas, controlling the discharge amount per unit time of the exhaust gas, applying non-combustible gas to the RTO 100, and stopping the supply of gas to the RTO 100 as the risk level gets higher from the first level to the fifth level.

According to an embodiment, the inflow amount per unit time of inflow gas may be controlled by controlling the inflow valve according to risk level to reduce the amount of inflow gas introduced to the RTO 100. For example, when the risk level is greater than or equal to a predetermined level, the inflow amount per unit time of inflow gas may decrease to a predetermined value or below, or the inflow amount per unit time of the inflow gas may decrease in inverse proportion to how high the risk level is during a predetermined time.

According to an embodiment, the component of the inflow gas may change by changing the inflow gas of a first component to the inflow gas of a second component according to the risk level. According to an embodiment, a plurality of gas pipes supplying inflow gas including different harmful gas may be connected to the inlet of the RTO 100. For example, a first gas pipe supplies a first inflow gas including volatile organic compounds and total hydrocarbon gas of high concentration as the main gas to be treated, and a second gas pipe supplies a second inflow gas including volatile organic compounds and total hydrocarbon gas of low concentration as the main gas to be treated. When the risk level is greater than or equal to a predetermined level, the processor 220 may control the gas valve of the first gas pipe to block the supply of the first inflow gas to the inlet of the RTO 100, and control the gas valve of the second gas pipe to start the supply of the second inflow gas to the inlet of the RTO 100, thereby changing the component of gas during a predetermined time period.

According to an embodiment, the discharge amount per unit time of exhaust gas may be controlled by controlling the gas valve in the outlet of the RTO 100 according to the risk level to increase the amount of discharge gas exhausted from the inside of the RTO 100 to the outside. For example, when the risk level is greater than or equal to a predetermined level, the discharge amount per unit time of exhaust gas may increase to a predetermined value or above, or the discharge amount per unit time of exhaust gas may increase in proportion to how high the risk level is during a predetermined time period.

According to an embodiment, non-combustible gas may be applied to the RTO 100 by temporarily supplying a predetermined specific non-combustible gas according to the risk level. According to an embodiment, non-combustible gas refers to a predetermined specific gas whose ignition temperature is greater than or equal to a predetermined value, which is very high, and thus has a low combustion possibility and low risk level. For example, a third gas pipe supplying non-combustible gas may be connected to the inlet of the RTO 100 or combustion chamber, and when the risk level is greater than or equal to a predetermined level, the processor 220 may lower the concentration ratio of ignition material and oxygen in the RTO 100 by controlling the gas valve of the third gas pipe to temporarily supply non-combustible gas in the RTO 100 for a predetermined time period.

With reference to FIG. 4, when the risk level is greater than or equal to a first level, the processor 220 may reduce the inflow amount per unit time of the inflow gas to a predetermined first value or below. When the risk level is greater than or equal to a second level, the processor 220 may change the component of inflow gas so that the inflow gas of a second component is introduced into the RTO 100, instead of the inflow gas of a first component. When the risk level is greater than or equal to a third level, the processor 220 may increase the discharge amount per unit time of the exhaust gas to a predetermined second value or above. When the risk level is greater than or equal to a fourth level, the processor 220 starts applying non-combustible gas to the RTO 100 in a predetermined value or above. When the risk level is greater than or equal to a fifth value, the inflow of inflow gas to RTO 100 may be stopped. According to an embodiment, the first level may be lower than the second level, the second level may be lower than the third level, the third level may be lower than the fourth level, and the fourth level may be lower than the fifth level.

According to an embodiment, the control value of inflow amount per unit time of inflow gas may decrease as the risk level increases. For example, as illustrated in FIG. 4, when the risk level increases from a normal level to the first to fifth levels, the risk level may be determined from a 1-1 value to 1-2 to 1-5 values (e.g., 1-1 value>1-2 value>1-3 value>1-4 value>1-5 value). Similarly, the control value of the discharge amount per unit time of exhaust gas increases as the risk level gets higher, and may be determined as illustrated in FIG. 4 (e.g., 2-1 value<2-2 value<2-3 value<2-4 value).

In other words, in reality, maintaining the load of the RTO 100 too low may deteriorate its efficiency, and thus even if the degree of risk increases by using various methods such as automatically stopping the supply according to the predicted risk level, or automatically changing the component of the supplied gas, the explosion risk of the RTO 100 may be minimized and the RTO 100 may be safely operated.

According to an embodiment, when it is determined to change the component of the inflow gas, the processor 220 may acquire gas scheduling information representing the component and the concentration of gas to be introduced to the RTO 100 according to the flow of time based on the history on inflow gas information and residual gas information during a predetermined time period, and control the component of inflow gas and the inflow amount per unit time according to gas scheduling information.

For example, the processor 220 may confirm the amount or the component of gas supplied in advance through the inflow gas information collected during a specific recent time period, and thus may generate gas scheduling information by distributing which gas is to be applied in which amount for each time period according to the prestored gas distribution algorithm. In case the risk level rises to a predetermined level or above while supplying volatile organic compound and total hydrocarbon of high concentration to the RTO 100 as the main gas to be treated through the first gas pipe, if the average concentration of the volatile organic compound and total hydrocarbon of high temperature is higher than a first reference value and a second reference value respectively in the inflow gas and the residual gas for the first hour, the processor 220 may perform gas control by generating gas scheduling information to supply the volatile organic compound and the total hydrocarbon of low concentration in a concentration of a third reference value (e.g., third reference value<first reference value and second reference value) to the RTO 100 as the main gas to be treated through the second gas pipe instead of the first gas pipe during the second hour.

According to an embodiment, the processor 220 may display gas monitoring information including inflow gas information, residual gas information and risk level. For example, the processor 220 may intuitively inform the current situation to a manager by displaying the risk level in real time through a display (not shown) included in the monitoring device 200, and effectively warn an emergent situation to the manager by displaying risk levels in different colors or outputting different warning messages and warning sound in different stages as the risk level gets higher.

According to an embodiment, when the risk level is greater than or equal to a predetermined first level, the processor 220 may output a warning sound, and when the risk level is greater than or equal to a predetermined second level which is higher than the first level, the processor 220 may provide a warning message requesting gas monitoring information and attention to the management device 300. In other words, when a problem is detected, the processor 220 may provide different warning output methods for each stage according to the risk level in case the RTO 100 is operating unreasonably at a high risk level.

According to an embodiment, when a user input for restarting the RTO 100 is received, the processor 220 may determine residual gas information including the component and the concentration of residual gas based on the history on inflow gas information and residual gas information for a predetermined time period, determine the restart risk level based on the determined residual gas information, and determine whether to restart the RTO 100 based on whether the restart risk level is greater than or equal to a predetermined level.

For example, when the operation of the RTO 100 is stopped by trouble, automatic control user input, etc., and a request for restarting combustion oxidation treatment of the RTO 100 is received according to user input, since there is no gas currently introduced, instead of acquiring inflow gas information, the processor 220 may analyze the gas composition condition and the amount of combustible gas inside the RTO 100 by using the component of the most recently introduced gas, inflow amount per unit time, component and concentration of residual gas, etc., and determine the restart risk level by calculating how different the concentration (e.g., 3%) of the combustible gas (e.g., propane gas) predicted to remain inside the current RTP 100 is from a predetermined explosion threshold range (e.g., 2.1% to 9.5%) corresponding to the corresponding combustible gas according to the analysis, and control the RTO 100 to operate the combustible equipment of the RTO 100 only when the restart risk level is determined to be in a safety level.

According to another embodiment, when a user input for restarting is received, the processor 220 may determine the restart risk level by receiving residual gas information from the sensor 210, and when the determined restart risk level is greater than or equal to a predetermined level, the processor 220 may determine to restart the RTO 100.

According to an embodiment, when the restart risk level is greater than or equal to a predetermined level, the processor 220 may discharge the exhaust gas for a predetermined time from the RTO 100 in an amount greater than or equal to a predetermined minimum value, or update the restart risk level after supplying a predetermined alternative gas (e.g., non-combustible gas, general atmospheric gas, inlet gas, etc.) to the RTO 100 in an amount greater than or equal to a predetermined minimum value, and when the updated restart risk level is less than a predetermined level, the processor 220 may determine to restart the RTO 100.

Accordingly, when restarting a combustion equipment of the RTO 100, the processor 220 may start restarting the combustion equipment only when it is analyzed to be safe by analyzing the amount of internal gas, and when it is analyzed not to be safe, the combustion equipment is restarted after discharging a minimum amount of internal gas or introducing a minimum amount of a relatively safer alternative gas, thereby improving safety.

According to an embodiment, the threshold for determining the risk level and restart risk level may be different. For example, a first threshold value, which is a reference value for the concentration of residual gas used for determining the risk level while determining whether to restart the RTO 100 when there is a request to restart the RTO 100 may be smaller than a second threshold value, which is a reference value for the concentration of residual gas used for determining the risk level while operating the combustion equipment of the RTO 100.

In other words, when the RTO 100 is stopped and then restarted, the uncertainty of predicting the concentration of the gas therein may be relatively high, and thus the risk possibility may be evaluated according to a more conservative judgment criterion by setting the reference value for determining the degree of risk to be smaller than usual.

According to an embodiment, the processor 200 may perform a series of operations for monitoring the RTO 100, may be implemented to comprise a central processor unit (CPU) for controlling the overall operation of the monitoring device 200, and may be electrically connected to the sensor 210 and other components or may be connected through a network to control the data flow therebetween.

In addition, a person having ordinary skill in the art may understand that the monitoring device 200 may further comprise other generally used components other than those illustrated in FIG. 2. For example, the monitoring device 200 may further comprise a communication module for transmitting and receiving information through a network, a storage module (e.g., memory, database, etc.) for storing data used throughout the operation, input/output interface, etc. for receiving user input or outputting information, etc. In addition, according to an embodiment, the monitoring device 200 may be implemented to comprise RTO 100.

Figure 5:
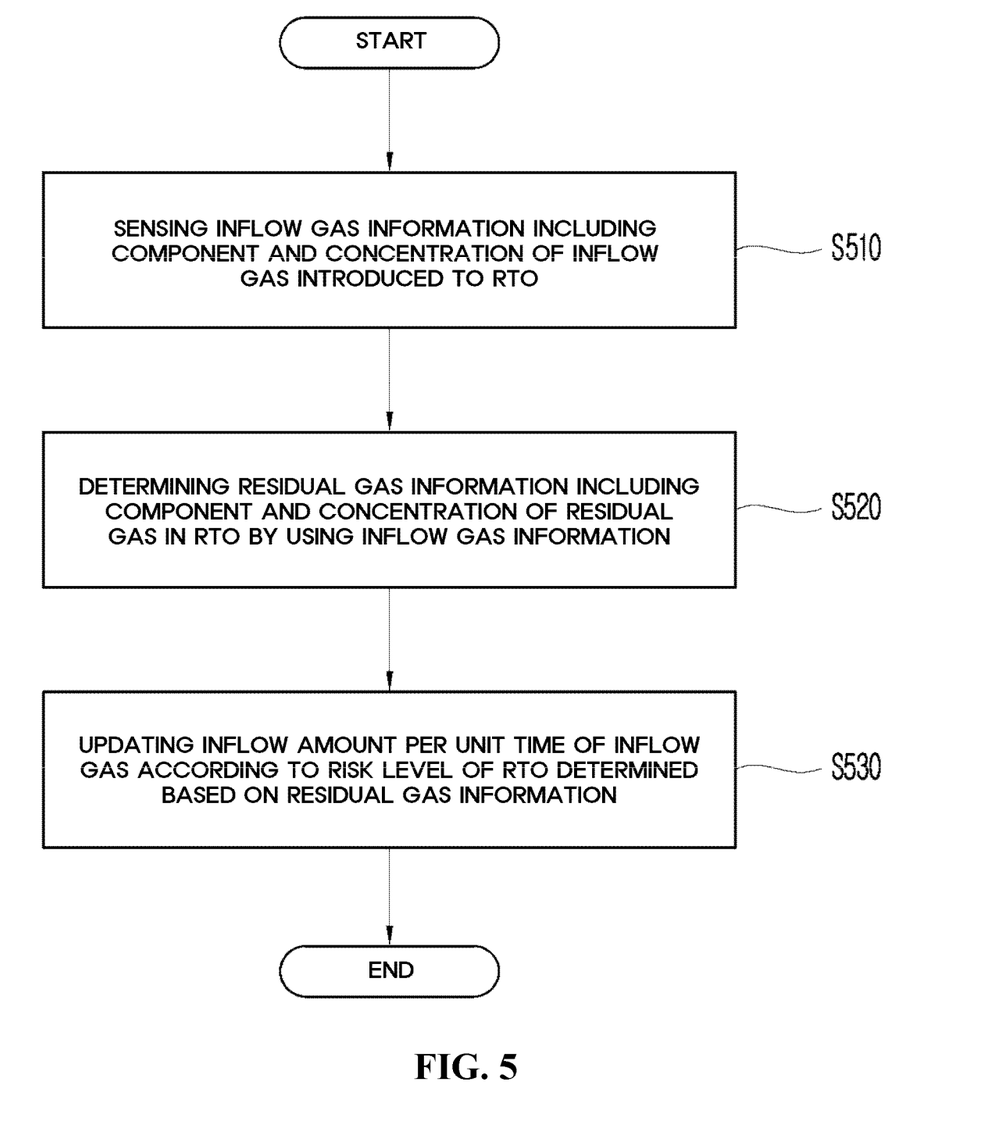
FIG. 5 is a flow chart illustrating how the monitoring device according to an embodiment monitors RTO.

FIG. 5 is a flow chart illustrating how the monitoring device 200 according to an embodiment monitors RTO 100.

With reference to FIG. 5, the monitoring device 200 in step S510 may sense the inflow gas information including the component and the concentration of the inflow gas introduced to the RTO 100. According to an embodiment, the monitoring device 200 may acquire information on the compound (e.g., volatile organic compound and hydrocarbon gas) and the concentration (e.g., amount of volatile organic compound gas per unit area) (e.g., 2,500 $\mu g/Sm^3$) of the harmful gas introduced into the RTO 100 through a sensor 210 disposed at an inlet of the RTO 100 and store and manage the same in a predetermined time period.

The monitoring device 200 in step S520 may determine the residual gas information including the component and the concentration of the residual gas in the RTO 100 by using the inflow gas information. According to an embodiment, the monitoring device 200 may analyze the inflow amount per unit time, the change in inflow amount per unit time, and immediately preceding concentration for each component of residual gas (e.g., concentration of the most recently predicted residual gas, initial setting value, etc.) for each gas component, and calculate a predicted value for the component and the concentration of the residual gas.

The monitoring device 200 in step S530 may update the inflow amount per unit time of inflow gas according to the risk level of RTO 100 determined based on the residual gas information. According to an embodiment, when the risk level is greater than or equal to a predetermined level, the monitoring device 200 may reduce the inflow amount per unit time of inflow gas introduced to the RTO 100 to a predetermined value corresponding to the risk level or below.

According to an embodiment of the present invention, when a problem is sensed by monitoring the condition of gas introduced to RTO 100 in real time, gas may be stably supplied in a way reducing the inflow amount of gas supplied to the RTO 100 so that the concentration of combustible gas in the RTO 100 is maintained below a lower explosive limit, and the potential explosion possibility may be minimized by maintaining the load of the RTO 100 to be low.

The present invention provides a sensor-based monitoring device for preventing explosion accidents of RTO, and the monitoring device 200 may comprise a sensor-based monitoring device for preventing explosion accidents of RTO.

Meanwhile, the above-described method can be written as a program that can be executed in a computer, it can be implemented in a general-purpose digital computer to operate the program using a computer-readable recording medium. In addition, the structure of the data used in the above-described method can be recorded on the computer-readable recording medium through various means. The computer-readable recording medium may include a storage medium such as a magnetic storage medium (for example, a ROM, a RAM, a USB, a floppy disk, a hard disk, etc.) and an optical reading medium (for example, a CD-ROM, a DVD, etc.).

The foregoing description of the present invention has been presented for illustrative purposes, and it is apparent to a person having ordinary skill in the art that the present invention can be easily modified into other detailed forms without changing the technical idea or essential features of the present invention. Therefore, it should be understood that the forgoing embodiments are by way of example only, and are not intended to limit the present disclosure. For example, each component which has been described as a unitary part can be implemented as distributed parts. Likewise, each component which has been described as distributed parts can also be implemented as a combined part.

The scope of the present invention is presented by the accompanying claims, and it should be understood that all changes or m modifications derived from the definitions and scopes of the claims and their equivalents fall within the scope of the present invention.

The invention claimed is:

1. A monitoring device, comprising:
a sensor configured to sense inflow gas information including a component and a concentration of an inflow gas introduced into a regenerative thermal oxidizer (RTO);
a memory configured to store instructions; and
a processor configured to be communicatively coupled to the sensor and the memory, and the processor by executing the instructions in the memory, determines residual gas information including a component and a concentration of a residual gas in the RTO by using the inflow gas information, and updates an inflow amount per unit time of the inflow gas according to a risk level of the RTO determined by the processor based on the residual gas information.

2. The monitoring device of claim 1, wherein the processor, by executing the instructions in the memory, determines whether the risk level is greater than or equal to a predetermined level based on whether a concentration of a predetermined specific gas among the residual gas satisfies a predetermined first condition, or whether an inflow increase amount per unit time of the inflow gas satisfies a predetermined second condition.

3. The monitoring device of claim 2, wherein when the risk level is greater than or equal to the predetermined level, the processor, by executing the instructions in the memory, transmits a control signal for reducing the inflow amount per unit time of the inflow gas to a level equal to or lower than a predetermined value corresponding to the risk level to an inflow valve which is configured to adjust an amount of the inflow gas.

4. The monitoring device of claim 1, wherein the processor, by executing the instructions in the memory, determines at least one of controlling the inflow amount per unit time of the inflow gas, changing the component of the inflow gas, controlling a discharge amount per unit time of an exhaust gas discharged from the RTO, applying a non-combustible gas to the RTO, and stopping a supply of the inflow gas to the RTO according to the risk level.

5. The monitoring device of claim 4, wherein a priority is granted by the processor which executes the instructions in the memory, in the order of controlling the inflow amount per unit time of the inflow gas, applying the non-combustible gas, changing the component of the inflow gas, controlling the discharge amount per unit time of the exhaust gas, and stopping the supply of the inflow gas.

6. The monitoring device of claim 4, wherein when it is determined to change the component of the inflow gas, the processor, by executing the instructions in the memory, acquires gas scheduling information representing a component and a concentration of a gas to be introduced into the RTO according to a time flow based on a history on the inflow gas information and the residual gas information for a predetermined time period, and controls the component of the inflow gas and the inflow amount per unit time according to the gas scheduling information.

7. The monitoring device of claim 1, wherein when a user input for restarting the RTO is received, the processor, by executing the instructions in the memory, determines the residual gas information based on a history on the inflow gas information and the residual gas information for a predetermined time period, determines a restart risk level based on the residual gas information, and determines whether to restart the RTO based on whether the restart risk level is greater than or equal to a predetermined level.

* * * * *